(12) United States Patent
Brasola et al.

(10) Patent No.: US 12,162,815 B2
(45) Date of Patent: Dec. 10, 2024

(54) CRYSTALLINE 2-FLUORO-3-NITROTOLUENE AND PROCESS FOR THE PREPARATION THEREOF

(71) Applicants: F.I.S.—Fabbrica Italiana Sintetici S.P.A., Montecchio Maggiore Vicenza (IT); AMGEN INC., Thousand Oaks, CA (US)

(72) Inventors: Elena Brasola, Montecchio Maggiore Vicenza (IT); Marco Di Silvestro, Montecchio Maggiore Vicenza (IT)

(73) Assignees: F.I.S.—FABBRICA ITALIANA SINTETICI S.P.A., Montecchio Maggiore Vicenza (IT); AMGEN INC., Thousand Oaks, CA (US)

( * ) Notice: Subject to any disclaimer, the term of this patent is extended or adjusted under 35 U.S.C. 154(b) by 925 days.

(21) Appl. No.: 17/258,385

(22) PCT Filed: Jul. 3, 2019

(86) PCT No.: PCT/EP2019/067894
§ 371 (c)(1),
(2) Date: Jan. 6, 2021

(87) PCT Pub. No.: WO2020/011626
PCT Pub. Date: Jan. 16, 2020

(65) Prior Publication Data
US 2021/0292271 A1     Sep. 23, 2021

(30) Foreign Application Priority Data
Jul. 9, 2018   (EP) ..................... 18182368

(51) Int. Cl.
*C07C 205/12*   (2006.01)
*C07C 201/16*   (2006.01)

(52) U.S. Cl.
CPC .......... *C07C 205/12* (2013.01); *C07C 201/16* (2013.01); *C07B 2200/13* (2013.01)

(58) Field of Classification Search
CPC ................ C07C 205/12; C07C 201/16; C07B 2200/13; C07D 213/75
See application file for complete search history.

(56) References Cited

U.S. PATENT DOCUMENTS 7,507,735 B2   3/2009   Morgan et al.
8,101,617 B2   1/2012   Morgan et al.
(Continued)

FOREIGN PATENT DOCUMENTS

CN   101177400 A   5/2008
EP      1982982 A1   10/2008
(Continued)

OTHER PUBLICATIONS

U.S. Appl. No. 15/898,303, filed Feb. 16, 2018, by William Brett Caldwell et al. (The U.S. Patent Application is not submitted herewith pursuant to the waiver of 37 C.F.R. § 1.98(a)(2)(iii) issued by the Office on Sep. 21, 2004.).
(Continued)

*Primary Examiner* — Jafar F Parsa
(74) *Attorney, Agent, or Firm* — MORRISON & FOERSTER LLP

(57) ABSTRACT

The present invention refers to a crystalline 2-fluoro-3-nitrotoluene compound of formula (I), and a process for the preparation thereof. Furthermore, the present invention relates to a process for the synthesis of a compound of formula (II) or salts thereof by means of the crystalline 2-fluoro-3-nitrotoluene.

17 Claims, 5 Drawing Sheets

(56) References Cited

U.S. PATENT DOCUMENTS

| | | |
|---|---|---|
| 8,110,595 B2 | 2/2012 | Morgan et al. |
| 8,445,495 B2 | 5/2013 | Morgan et al. |
| 8,513,257 B2 | 8/2013 | Morgan et al. |
| 8,871,768 B2 | 10/2014 | Morgan et al. |
| 8,871,769 B2 | 10/2014 | Morgan et al. |
| 9,150,564 B2 | 10/2015 | Morgan et al. |
| 9,643,925 B2 | 5/2017 | Morgan et al. |
| 9,895,308 B2 | 2/2018 | Caldwell |
| 9,951,015 B2 | 4/2018 | Bi et al. |
| 9,988,354 B2 | 6/2018 | Cui et al. |
| 10,035,770 B2 | 7/2018 | Morgan et al. |
| 10,385,023 B2 | 8/2019 | Morgan et al. |
| 10,421,726 B2 | 9/2019 | Bi et al. |
| 10,543,215 B2 | 1/2020 | Scott et al. |
| 10,975,034 B2 | 4/2021 | Morgan et al. |
| 11,040,956 B2 | 6/2021 | Caille et al. |
| 11,465,969 B2 | 10/2022 | Morrison et al. |
| 11,576,910 B2 | 2/2023 | Honarpour et al. |
| 11,702,380 B2 | 7/2023 | Caille et al. |
| 11,753,394 B2 | 9/2023 | Caille et al. |
| 11,884,630 B2 | 1/2024 | Bi et al. |
| 11,926,592 B2 | 3/2024 | Morrison |
| 11,931,358 B2 | 3/2024 | Honarpour |
| 11,958,809 B2 | 4/2024 | Cui |
| 2006/0014761 A1 | 1/2006 | Morgan et al. |
| 2007/0161617 A1 | 7/2007 | Morgan et al. |
| 2009/0036447 A1 | 2/2009 | Morgan et al. |
| 2009/0099198 A1 | 4/2009 | Morgan et al. |
| 2010/0029680 A1 | 2/2010 | Morgan et al. |
| 2012/0172372 A1 | 7/2012 | Morgan et al. |
| 2013/0324549 A1 | 12/2013 | Morgan et al. |
| 2014/0038983 A1 | 2/2014 | Morgan et al. |
| 2014/0309235 A1 | 10/2014 | Bi et al. |
| 2015/0005296 A1 | 1/2015 | Morgan et al. |
| 2016/0015628 A1 | 1/2016 | Caldwell |
| 2016/0016906 A1 | 1/2016 | Cui et al. |
| 2016/0115133 A1 | 4/2016 | Morgan et al. |
| 2017/0267638 A1 | 9/2017 | Morgan et al. |
| 2018/0140611 A1 | 5/2018 | Scott et al. |
| 2018/0273479 A1 | 9/2018 | Bi et al. |
| 2018/0305316 A1 | 10/2018 | Morgan et al. |
| 2018/0312469 A1 | 11/2018 | Cui et al. |
| 2019/0352267 A1 | 11/2019 | Morgan et al. |
| 2020/0079736 A1 | 3/2020 | Cui et al. |
| 2020/0108076 A1 | 4/2020 | Scott et al. |
| 2020/0155547 A1 | 5/2020 | Honarpour et al. |
| 2020/0277261 A1 | 9/2020 | Bi et al. |
| 2020/0308143 A1 | 10/2020 | Caille et al. |
| 2020/0331859 A1 | 10/2020 | Cui et al. |
| 2020/0399221 A1 | 12/2020 | Cui et al. |
| 2021/0198203 A1 | 7/2021 | Morgan et al. |
| 2021/0221772 A1 | 7/2021 | Man et al. |
| 2022/0042055 A1 | 2/2022 | Bisagni et al. |
| 2022/0184068 A1 | 6/2022 | Honarpour et al. |
| 2022/0185779 A1 | 6/2022 | Morgan et al. |
| 2023/0044617 A1 | 2/2023 | Cui et al. |
| 2023/0090391 A1 | 3/2023 | Bi et al. |
| 2023/0149394 A1 | 5/2023 | Honarpour et al. |
| 2023/0373955 A1 | 11/2023 | Caille et al. |
| 2024/0101517 A1 | 3/2024 | Cui |
| 2024/0199550 A1 | 6/2024 | Morrison |

FOREIGN PATENT DOCUMENTS

| | | |
|---|---|---|
| EP | 2172198 A1 | 4/2010 |
| WO | 2007/091736 A1 | 8/2007 |
| WO | 2009/014100 A1 | 1/2009 |
| WO | 2014/152236 A1 | 9/2014 |
| WO | 2014/152270 A1 | 9/2014 |
| WO | 2019/006231 A1 | 1/2019 |

OTHER PUBLICATIONS

U.S. Appl. No. 17/176,003, filed Feb. 15, 2021, by Sheng Cui et al. (The U.S. Patent Application is not submitted herewith pursuant to the waiver of 37 C.F.R. § 1.98(a)(2)(iii) issued by the Office on Sep. 21, 2004.).

U.S. Appl. No. 17/263,224, filed Jan. 26, 2021, by Henry Morrison et al. (The U.S. Patent Application is not submitted herewith pursuant to the waiver of 37 C.F.R. § 1.98(a)(2)(iii) issued by the Office on Sep. 21, 2004.).

U.S. Appl. No. 17/309,727, filed Jun. 16, 2021, by Serena Bisagni et al. (The U.S. Patent Application is not submitted herewith pursuant to the waiver of 37 C.F.R. § 1.98(a)(2)(iii) issued by the Office on Sep. 21, 2004.).

U.S. Appl. No. 17/324,867, filed May 19, 2021, by Sebastien Caille et al. (The U.S. Patent Application is not submitted herewith pursuant to the waiver of 37 C.F.R. § 1.98(a)(2)(iii) issued by the Office on Sep. 21, 2004.).

Inukai, K et al. (1956). "Study on Difluoro-Substituted Malachite Green," the Journal of the Society of Chemical Industry, Japan, 59(10):1160-1163, with English Translation, 8 pages.

Nagasawa, H. (2007). "H119. Crystallization Manipulation When Producing Active Pharmaceutical Ingredients (Drugs Substances)," Collection of the Abstracts of the Research Presentations in the 39th General Meeting in Autumn of 2007, the Society of Chemical Engineers, Japan, H119, with English Translation, 4 pages.

Yamano, M. (Sep. 1, 2007). "Approaches to Crystal Polymorphism in Process Research for Drugs," Journal of Synthetic Organic Chemistry (Japan) 65(9):907-913. (English Translation), 14 pages.

International Application No. PCT/EP19/67894, International Search Report and Written Opinion, mailed Aug. 30, 2019.

International Application No. PCT/EP19/067894, International Preliminary Report on Patentability, mailed Jan. 21, 2021.

Julius et al., Berichte der Deutschen Chemichen Gesellschaft [Abteilung] B: Abhandlungen, 64B:2465-2473 (1931).

U.S. Appl. No. 18/421,849, filed Jan. 24, 2024, by Sheng Cui et al. (The U.S. Patent Application is not submitted herewith pursuant to the waiver of 37 C.F.R. § 1.98(a)(2)(iii) issued by the Office on Sep. 21, 2004.).

U.S. Appl. No. 18/531,424, filed Dec. 6, 2023, by Mingda Bi et al. (The U.S. Patent Application is not submitted herewith pursuant to the waiver of 37 C.F.R. § 1.98(a)(2)(iii) issued by the Office on Sep. 21, 2004.).

Figura 4 A
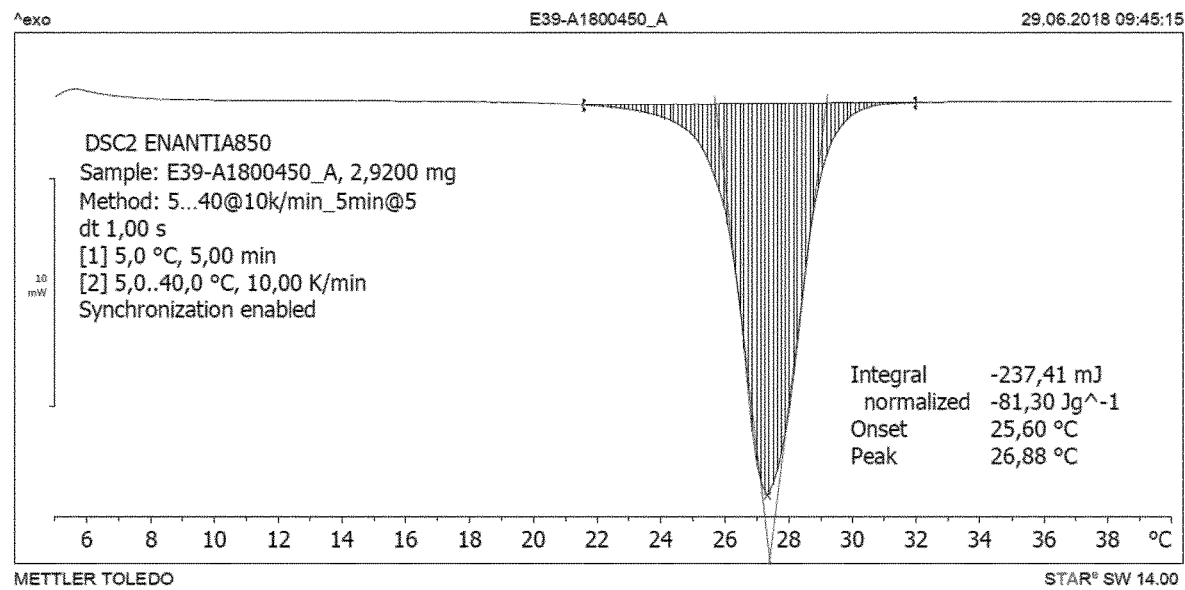
Figure 4 B
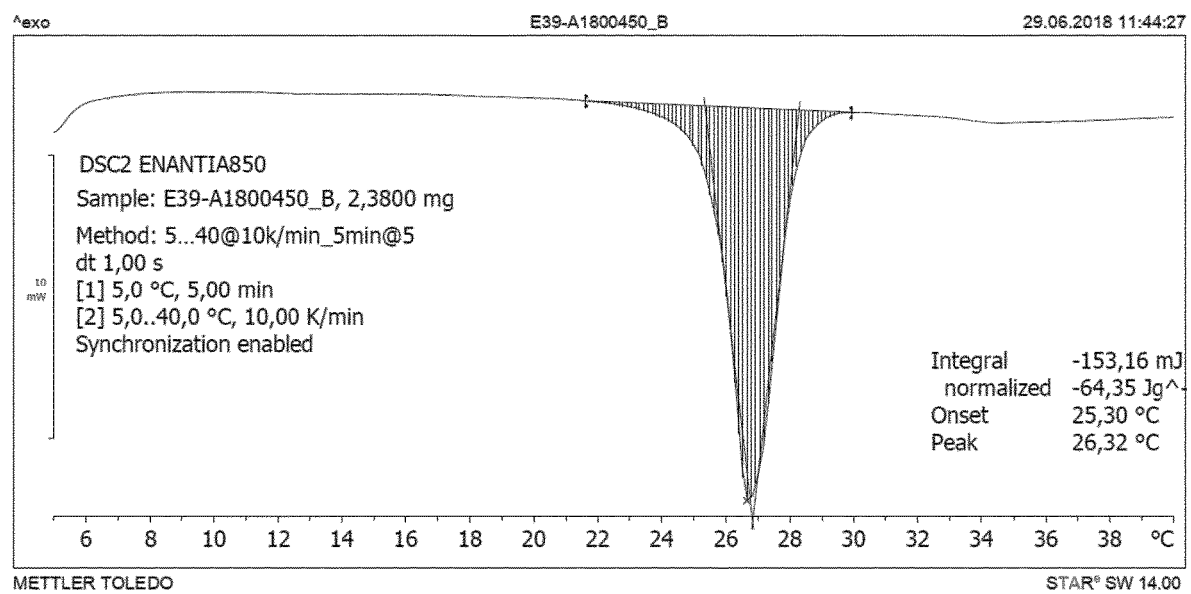

CRYSTALLINE 2-FLUORO-3-NITROTOLUENE AND PROCESS FOR THE PREPARATION THEREOF

TECHNICAL FIELD OF THE INVENTION

The present invention refers to a crystalline 2-fluoro-3-nitrotoluene (abbreviated FNT) compound of formula (I):

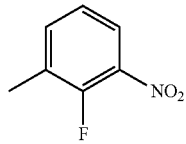

(I)

and a process for the preparation thereof. Furthermore, the present invention relates to a process for the synthesis of a compound of formula (II):

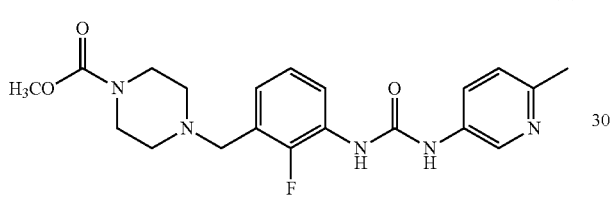

(II)

or salts thereof and the use of a crystalline 2-fluoro-3-nitrotoluene for the synthesis of the compound of formula (II) or salts thereof.

BACKGROUND OF THE INVENTION

Methods for preparing the compound 2-fluoro-3-nitrotoluene in the physical state of a liquid are known in the art and such liquid product is commercially available. Generally, such liquid compound is purified by distillation.

In particular, EP 2 172 198 A1 (corresponding to the international patent application WO2009014100 A1) discloses a preparation process of FNT starting from 2-chloro-3-nitrotoluene with cesium fluoride in dimethyl sulfoxide. The final FNT product is obtained as yellow oil and purified by reduced-pressure distillation (boiling point: 118° C. to 122° C./0.0197 atm).

WO2007091736 A1 discloses a preparation process of FNT with cesium chloride in dimethyl sulfoxide, the final product being obtained as yellow oil which is purified by reduced-pressure distillation (boiling point: 118° C. to 122° C./0.0197 atm).

Julius, V. et al., Berichte der Deutschen Chemichen Gesellschaft [Abteilung] B: Abhandlungen, Volume: 64B, Pages 2465-73, (1931), discloses a process for obtaining 2-fluoro-3-nitrotoluene from a 2-nitro compound with amyl nitrite through the 3-nitro-diazonium fluoroborate with sand (20-23% yield).

However, the handling of a liquid product and the purification process of a substance in the liquid form, generally by distillation, is considered to be complex, and potentially hazardous due to the nitrotoluenic nature of the concerned substance.

SUMMARY OF THE INVENTION

Therefore, the problem addressed by the present invention is to provide a crystalline form of 2-fluoro-3-nitrotoluene (FNT) which is easily purifiable and handable, wherein such crystalline form is also obtained with high yield.

This problem is solved by a crystalline form of 2-fluoro-3-nitrotoluene and a process for the preparation thereof by a specific purification process.

Further characteristics and advantages of the crystalline form and the corresponding preparation process according to the invention will become apparent from the below-reported description of preferred embodiments, given by way of a non-limiting example.

BRIEF DESCRIPTION OF THE DRAWINGS

FIGS. 3, 4A, 4B, 5A and 5B show the DSC for samples A1800449 (analysis B), A1800450 (analysis A and B) and A1800451 (analysis A and B), respectively.

DETAILED DESCRIPTION OF THE INVENTION

Figure 1:
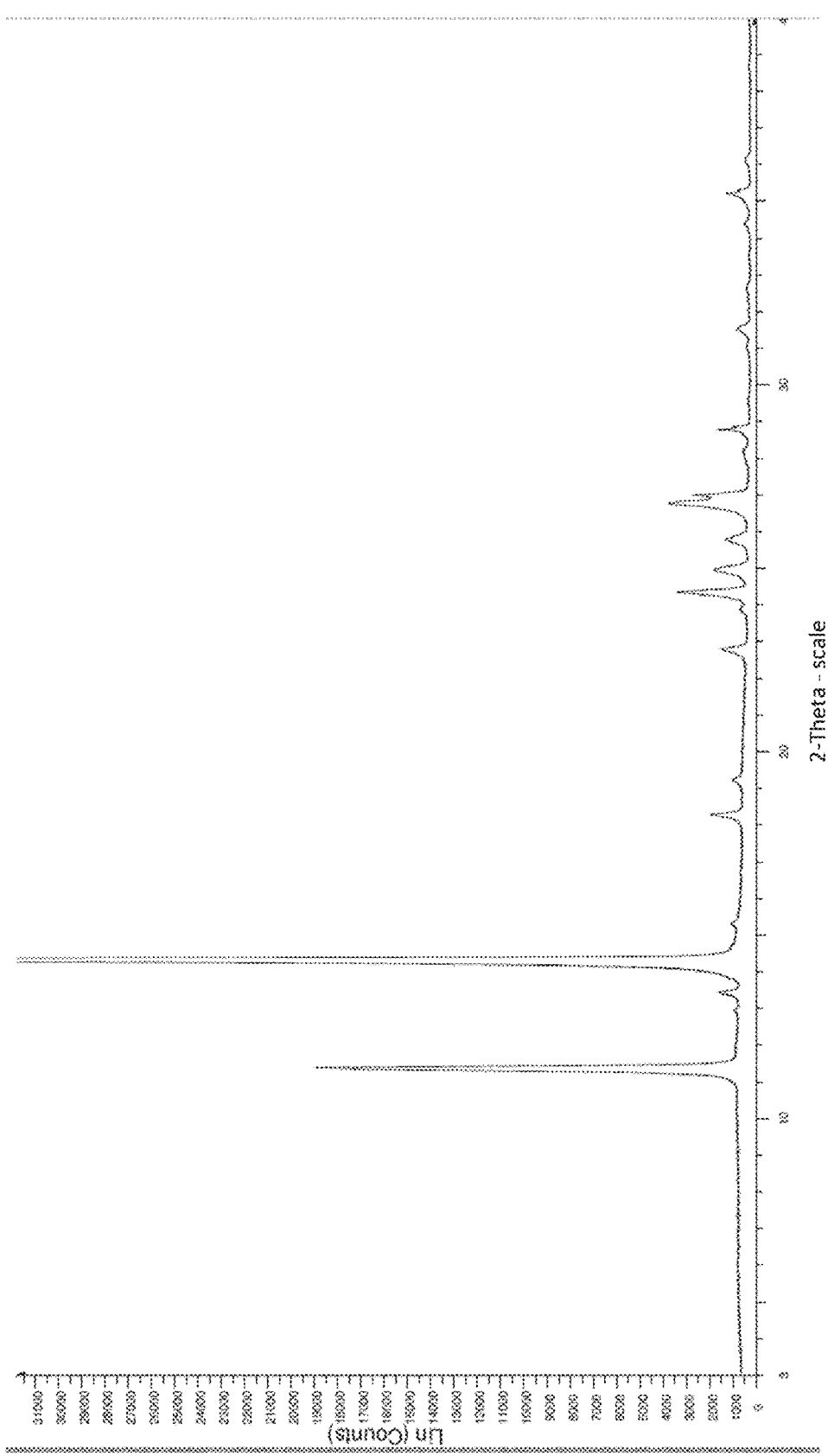
FIG. 1 shows the XPRD diffractogram of the crystalline solid form of 2-fluoro-3-nitrotoluene (FNT).

According to a first aspect, the present invention relates to crystalline 2-fluoro-3-nitrotoluene of formula (I):

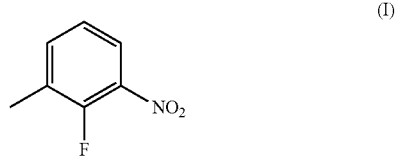

(I)

having a DSC onset peak at a value among 25.0 and 26.0° C. or having a DSC maximum peak at a value among 26.0 and 27.5° C. or having a characteristic X-ray powder diffraction pattern with characteristic peak expressed in 2-Theta values (2θ) at 14.3±0.2.

Advantageously, the Applicant has surprisingly found that obtaining 2-fluoro-3-nitrotoluene as crystalline solid by a purification process of crystallization, the complexity of its preparation is considerably reduced, as well as the handling of the crystalline form itself, is considerably improved. Furthermore, such new crystalline form is obtained with high yields (i.e., higher than 90%). Indeed, since the process provides a product with higher purity, it shows a well higher melting point, thus allowing the easy handling of the product.

As further advantage, the compound of formula (I) prepared according to the process of the invention has a reduced amount of isomer impurity 2-fluoro-4-nitrotoluene of formula:

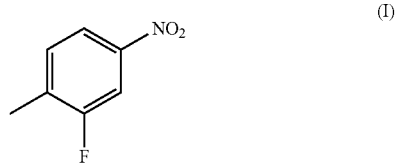

(I)

which is an impurity particularly difficult to be removed by distillation since it has similar boiling point of FNT and, since it reacts similarly to FNT, it generates isomer impurities into the products prepared starting from FNT. In particular, the process of the invention reduces the amount of said impurity as exemplified in example 4. For said purpose, the volume ratio methanol/H$_2$O 1:1 or methanol/water 2:1 is preferred.

According to a preferred embodiment, the crystalline 2-fluoro-3-nitrotoluene has a DSC onset peak at a value among 25.0 and 26.0° C. and/or a DSC maximum peak at a value among 26.0 and 27.5° C. and has a characteristic X-ray powder diffraction pattern with characteristic peak expressed in 2-Theta values (2θ) at 14.3±0.2.

According to another preferred embodiment, the crystalline 2-fluoro-3-nitrotoluene has a DSC onset peak at a value among 25.0 and 26.0° C. and a DSC maximum peak at a value among 26.0 and 27.5° C. and has a characteristic X-ray powder diffraction pattern with characteristic peak expressed in 2-Theta values (2θ) at 14.3±0.2.

According to another preferred embodiment, the crystalline 2-fluoro-3-nitrotoluene has a DSC onset peak at a value among 25.0 and 26.0° C. and a characteristic X-ray powder diffraction pattern with characteristic peak expressed in 2-Theta values (2θ) at 14.3±0.2.

Preferably, the crystalline 2-fluoro-3-nitrotoluene has a DSC maximum peak at a value among 26.0 and 27.5° C. and a characteristic X-ray powder diffraction pattern with characteristic peak expressed in 2-Theta values (2θ) at 14.3±0.2.

Preferably, the crystalline 2-fluoro-3-nitrotoluene has a DSC onset peak at a value among 25.0 and 26.0° C. and a DSC maximum peak at a value among 26.0 and 27.5° C.

Furthermore, the crystalline 2-fluoro-3-nitrotoluene can have a further peak at characteristic X-ray powder diffraction pattern expressed in 2-Theta values (2θ) at 11.3±0.2.

According to another preferred embodiment of the present invention, the crystalline 2-fluoro-3-nitrotoluene has a DSC onset peak at a value among 25.0 and 25.5° C.

Preferably, the crystalline 2-fluoro-3-nitrotoluene has a DSC maximum peak at a value among 26.5 and 27.2° C.

As for the mean of the term DSC onset peak, as commonly known by the skilled person, the extrapolated onset-temperature (according to DIN EN ISO 11357-1:2010-03) is the designed intersection point of the extrapolated baseline and the inflectional tangent at the beginning of the melting or crystallization peak. The baseline and the inflectional tangent are determined from the temperature-dependent heat flow signal. In the case of pure and homogeneous materials, the onset-temperature can be indicated as melting temperature. In contrast to peak-temperature, the onset-temperature is less dependent on heating rate and sample mass. Furthermore, onset-temperatures are usually used for temperature calibration of a DSC.

According to a further aspect, the present invention relates to a process for preparing a crystalline 2-fluoro-3-nitrotoluene of formula (I):

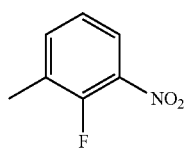

(I)

as defined above, wherein said process comprises the crystallization of the 2-fluoro-3-nitrotoluene of formula (I) from a mixture of water and solvent selected from a $C_1$-$C_3$ alcohol.

As intended herein, the expression $C_1$-$C_3$ alcohol means methanol, ethanol, iso-propanol, n-propanol, respectively.

According to a preferred embodiment, the process further comprises a stirring step. Advantageously, involving a stirring step it is possible to obtain crystals with higher particle size, which allows faster filtrations of the suspensions containing the product of formula (I).

Preferably, the mixture of water and solvent, preferably a $C_1$-$C_3$ alcohol, more preferably methanol or ethanol, even more preferably methanol, is stirred for a period of time longer than 10 min., more preferably longer than 30 min. Preferably the mixture of water and solvent is stirred for a period of time from 30 min to 4 hours, more preferably from 1 hour to 3 hours, even more preferably about 2 hours. Preferably the stirring is carried out at a temperature from 0° C. to 30° C., preferably from 5° C. to 25° C., even more preferably from 10° C. to 20° C.

According to another preferred embodiment, the mixture of water and solvent, preferably a $C_1$-$C_3$ alcohol, more preferably methanol or ethanol, even more preferably methanol, is stirred for a period of time from 30 min to 4 hours, preferably from 1 hour to 3 hours, more preferably about 2 hours, at a temperature from 0° C. to 30° C., preferably from 5° C. to 25° C., more preferably from 10 to 20° C.

According to another preferred embodiment, the mixture is a mixture of water and methanol is stirred for a period of time from 1 hour to 3 hours at a temperature from 5 to 25° C., preferably from 10 to 20° C.

As it will be evident for the skilled person, the preparation and the handling of the crystalline form of the invention is advantageously easier compared to the one of other physic forms, such as compounds in the liquid form (e.g. oils, liquid with oily consistency). Furthermore, since the purification process of the present invention is represented by the crystallization itself, complex purifying steps such as, for example, distillation can be avoided.

According to a preferred embodiment of the present invention, the process is carried out by dissolving a 2-fluoro-3-nitrotoluene into a solvent selected from a $C_1$-$C_3$ alcohol, preferably methanol and ethanol, even more preferably methanol, and then adding water as antisolvent.

With reference to the volume ratio between the solvent and water, a ratio from 3:1 to 1:3 can be provided. Preferably the volume ratio between the solvent and water is 1:1 or 2:1, being 1:1 more preferred.

According to another particularly preferred embodiment, the $C_1$-$C_3$ alcohol is methanol or ethanol, preferably, methanol and the volume ratio between the solvent and water is 1:1.

As intended herein, the term volumes means volume of solvent per unit of product, thus, for example, 1 volume is 1 Liter per 1 Kilo, or 1 mL for 1 gram, or 1 microliter per 1 milligram. Thus, 10 volumes means for example 10 liters per 1 Kilogram of substance, in this case the solvent and water used in the mixture of solvent and water used in the preparation of the a crystalline 2-fluoro-3-nitrotoluene of formula (I).

As far as the volumes of each solvent and water used in the mixture of solvent and water used in the preparation of the crystalline 2-fluoro-3-nitrotoluene of formula (I), preferably from 1 to 10 volumes, more preferably from 1 to 5 volumes, even more preferably 2 volumes, can be used.

According to an alternative embodiment of the invention, the crystalline 2-fluoro-3-nitrotoluene of formula (I):

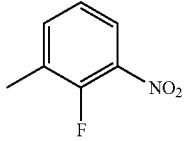

(I)

as defined above, can be prepared according to a process comprising the steps of:

- adding the compound of formula (I) as a liquid to a mixture of water and solvent $C_1$-$C_3$ alcohol as defined above;
- heating said mixture up to achieve a complete homogenization;
- cooling the resulting solution. After the cooling step, a further steps of stirring and filtration of the suspension of the compound of formula (I) can be carried out.

According to a further aspect, the present invention relates to a process for the synthesis of a compound of formula (II):

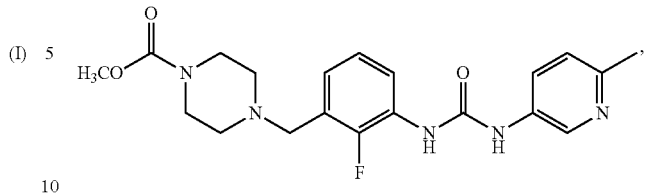

(II)

or salts thereof, wherein said process comprises the steps of:

preparing a crystalline 2-fluoro-3-nitrotoluene of formula (I):

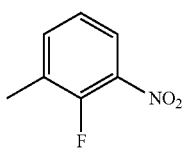

(I)

as defined above according to a process as defined above;

converting said crystalline 2-fluoro-3-nitrotoluene into the compound of formula (II).

The conversion step from the crystalline 2-fluoro-3-nitrotoluene to the compound of formula (II) can be carried out according to the teachings of pages from 15 to 18 and from 21 to 28 of WO2014/152270.

According to a further aspect, a crystalline 2-fluoro-3-nitrotoluene of formula (I) as defined above can be used for the synthesis of the compound of formula (II):

(II)

or salts thereof.

Experimental Section

All the raw materials are commercially available, for example by Sigma-Aldrich.

For the synthesis of the 2-fluoro-3-nitrotoluene to be crystallized through the process of the present invention can be used any process known in the art. For instance, it can be prepared according to the procedures disclosed in CN 101177400A, WO2009014100 (par. 657).

Example 1—Purification by Crystallization

A 4-neck round bottom flask was charged with 150 g of the 2-fluoro-3-nitrotoluene (FNT) of formula:

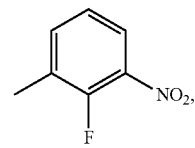

obtained by the process disclosed in WO2009014100, and dissolved in methanol 300 ml (2 V) at a temperature of 30° C. The homogeneous solution was cooled to 17/18° C. Water 300 ml (2 V) was dosed over 2 h at 17-19° C. The solution was stirred for 2 hours at 15° C. thus obtaining a suspension of the product which, upon filtration (fast filtration and clear mother liquor) at 15° C. and subsequent wash (MeOH/H$_2$O (0,5 V/0,5 V) and drying under vacuum, provides a crystal solid compound (I) with 90% yield, wherein XPRD diffractogram of the solid form is reported in FIG. 1 and the corresponding data are also reported in the following table 1.

TABLE 1

| Angle (2-θ° ± 0.1) | Intensity (%) |
|---|---|
| 11.341 | 19.4 |
| 12.902 | 0.9 |
| 13.409 | 1.6 |
| 14.299 | 100.0 |
| 15.295 | 1.0 |
| 18.265 | 1.9 |
| 19.215 | 1.0 |
| 22.780 | 1.4 |
| 23.889 | 0.7 |
| 24.342 | 3.4 |
| 24.963 | 1.8 |
| 25.787 | 1.3 |
| 26.785 | 3.8 |
| 26.987 | 2.7 |
| 28.195 | 0.5 |
| 28.807 | 1.6 |
| 29.565 | 0.3 |
| 31.058 | 0.4 |
| 31.544 | 0.7 |

TABLE 1-continued

| Angle (2-θ° ± 0.1) | Intensity (%) |
|---|---|
| 32.655 | 0.4 |
| 34.416 | 0.4 |
| 35.221 | 1.3 |
| 36.137 | 0.4 |

Figure 2:
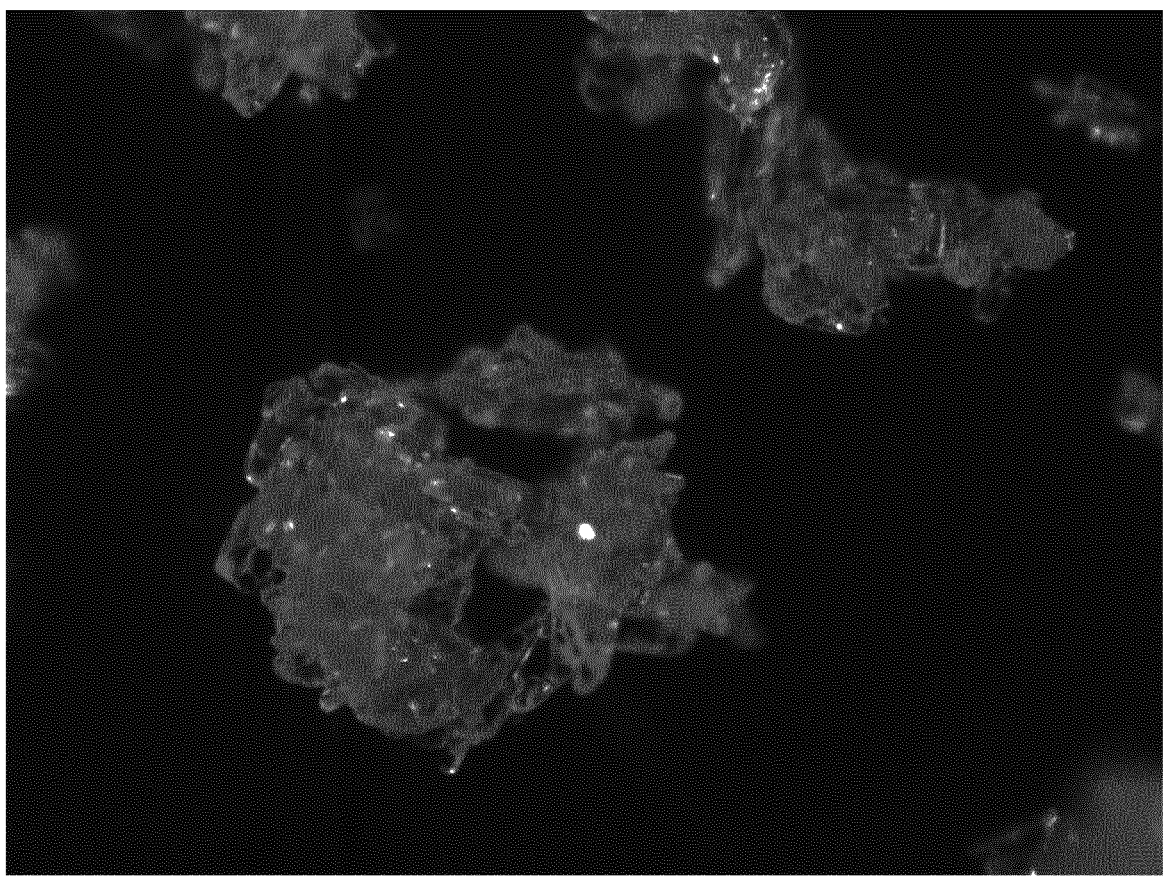
FIG. 2 is an optical microscopy photo (4×) of the crystalline solid form of 2-fluoro-3-nitrotoluene (FNT).
Figure 3:
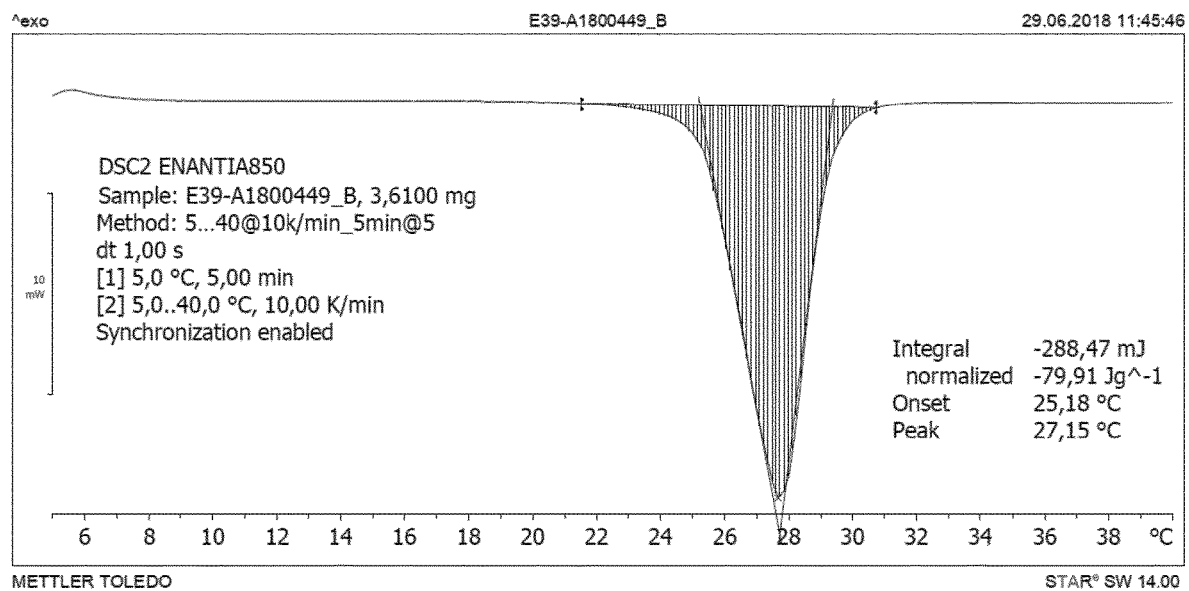
Figure 5:
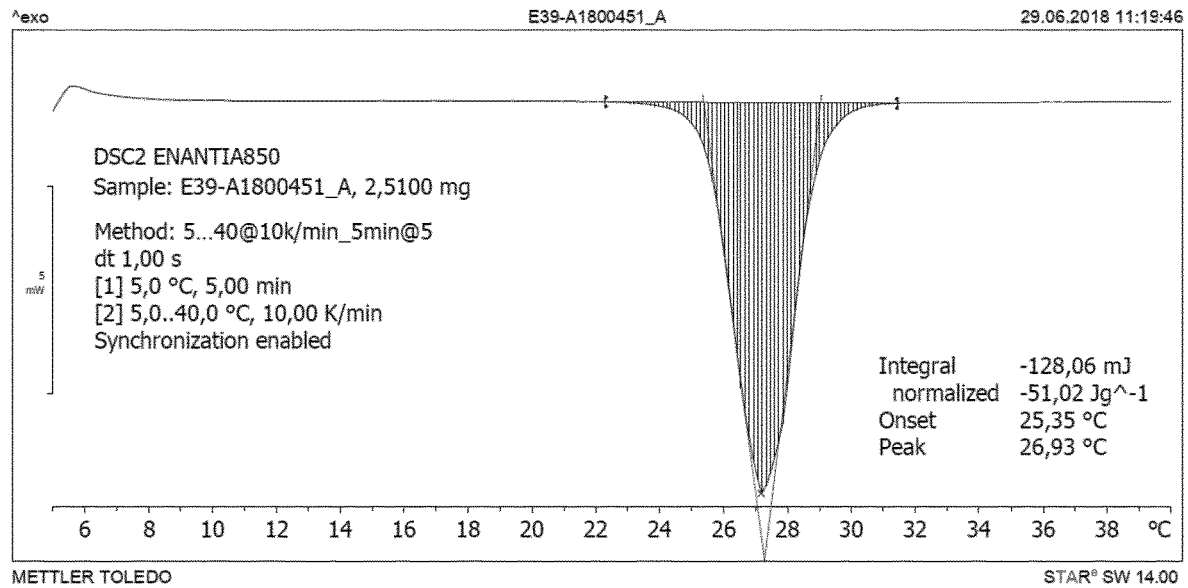
Figure 5:
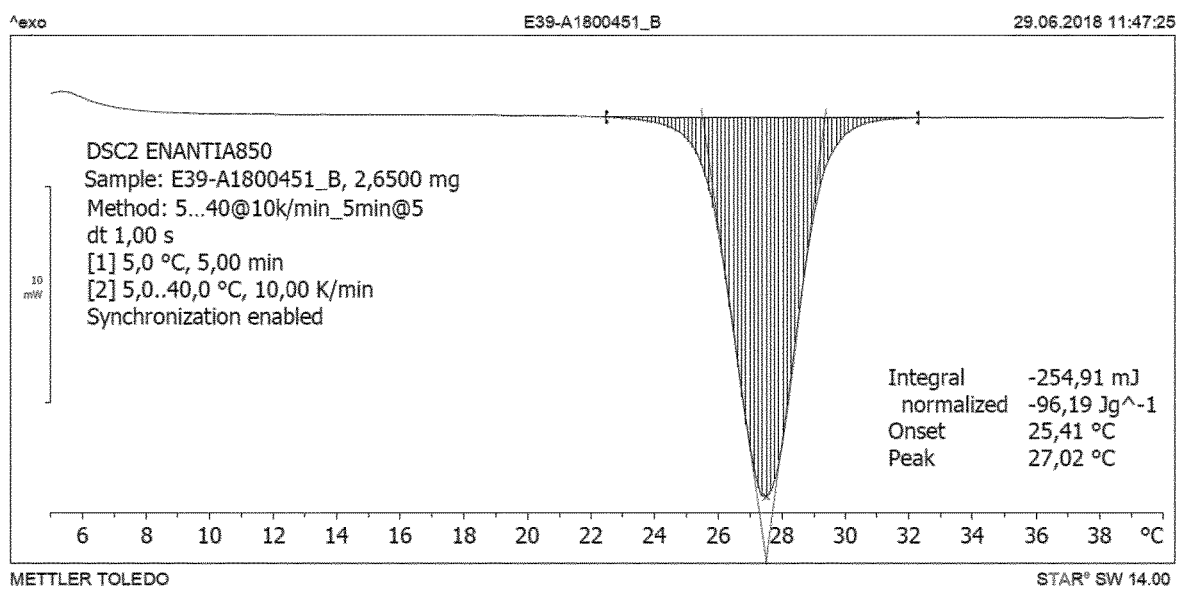

The solid crystalline of 2-fluoro-3-nitrotoluene (FNT) obtained is shown in FIG. 2, wherein an optical microscopy photo (4×) is reported.

Example 2—Purification by Crystallization

Example 1 was repeated by using the same overall volume of the solvent and water and having volume ratio between methanol and water of 2:1 and 1:2, thus obtaining yields of 80% and 88%, respectively.

Example 3—Purification by Crystallization

Example 1 was repeated by using ethanol instead of methanol, and a yield of 88% was obtained.

Example 4—Correlation Between Purification and Solvent/Water Volume Ratios

Experimental tests were carried out in order to assess the correspondence between the purity of the product obtained and the purification and solvent/water volume ratios used. The following table 2 shows the results obtained.

TABLE 2

| Sample | "crude" FNT (starting material) | Purified FNT (MeOH/H$_2$O 1/1) | Purified FNT (MeOH/H$_2$O 2/1) | Purified FNT (MeOH/H$_2$O 1/2) |
|---|---|---|---|---|
| Purity (A %) | 95.5% | 97.4% | 97.3% | 96.7% |
| 2-F,4-NO$_2$ toluene isomer | 0.13% | 0.07% | 0.07% | 0.09% |
| 2-F,5-NO$_2$ toluene isomer | 3.43% | 2.13% | 2.21% | 2.69% |
| Max unknown | 0.18% (RRT 1.25) | 0.12% (RRT 1.25) | 0.12% (RRT 1.25) | 0.14% (RRT 1.25) |

Example 5—DSC Analysis

Samples of 2-fluoro-3-nitrotoluene (A1800449, A1800450 and A1800451) were stored at 4° C. before DSC analysis. The solids were gently milled at 4° C. to obtain a homogeneous powder suitable for DSC analysis. Then, DSC sample preparation was performed in a temperature controlled cool chamber at 17.0±0.5° C. to avoid any possible sample melting. DSC analyses were recorded with a Mettler Toledo DSC2. NF-Tol samples were weighed at ca. 17° C. into a 40 μL aluminium crucible with a pinhole lid and heated at 10K/min from 5 to 40° C. under nitrogen (50 ml/min). For each batch, duplicate analyses were performed (A and B). A sample was also analysed at 5K/min from 5 to 40° C. under nitrogen (50 mL/min) to check possible effect of the heating rate, but a similar DSC profile was obtained. The results of these analyses are summarized in the following table 3 below. The DSCs performed are reported in FIGS. 3, 4A, 4B, 5A and 5B.

TABLE 3

| Batch | Analysis | Peak max ° C. | Peak onset ° C. | Peak onset mean ° C. |
|---|---|---|---|---|
| A1800449 | B | 27.2 | 25.2 | — |
| A1800450 | A | 26.9 | 25.6 | 25.5 |
|  | B | 26.3 | 25.3 |  |
| A1800451 | A | 26.9 | 25.4 | 25.4 |
|  | B | 27.0 | 25.4 |  |

Example 6—XPRD Method

As far as the XPRD method is concerned, the instrument, the instrumental parameters and the other parameters used are reported in table 4 below. The XPRD diffractogram of FNT obtained is reported in FIG. 1.

TABLE 4

| Instrument | : X-ray diffractometer D8 ADVANCE (Bruker) |
|---|---|
| Instrumental parameters | |
| Scan | : 1. From 3.00° to 40.00° |
| Source | : Cu; 35 mA, 50 KV |
| Radiations | : K(α1) e K(α2) |
| primary optic settings | : 1. 20 mm programmable slit<br>2. 2.3° Soller<br>3. Distance sample-detector 217 mm |
| secondary optic settings | : 1. Nickel filter, 0.5 mm thickness<br>2. 1.5° Soller<br>3. 3 mm slit<br>4. Distance sample-detector 217 mm |
| Detector | : PSD detector (model Lynx eye, Bruker) |
| Operative conditions of detector | Scan from 3.0° to 40.0°, step size 0.015°, collection time 0.5 sec per step and PSD window 0.8° |
| Other parameters | |
| Sample holder | : 1. round in polycarbonate with dome, rotating<br>2. dimensions: diameter 25 mm and depth 1 mm |

The invention claimed is:
1. A process for the synthesis of a compound of formula (II):

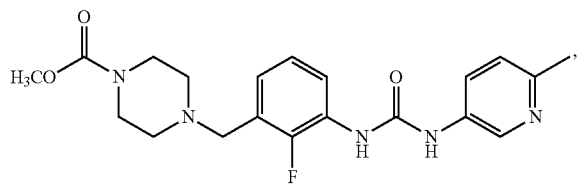

or a salt thereof,
wherein said process comprises the steps of:
preparing crystalline 2-fluoro-3-nitrotoluene of formula (I):

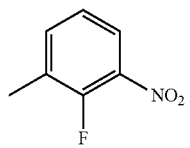

according to a process which comprises crystallization of the 2-fluoro-3-nitrotoluene of formula (I) from a mixture of water and a solvent selected from a $C_1$-$C_3$ alcohol, wherein the crystalline 2-fluoro-3-nitrotoluene of formula (I) has a DSC onset peak at a value among 25.0 and 26.0° C. or a DSC maximum peak at a value among 26.0 and 27.5° C. or an X-ray powder diffraction pattern comprising a peak expressed in 2-Theta values (2θ) at 14.3±0.2; and converting said crystalline 2-fluoro-3-nitrotoluene into the compound of formula (II), or a salt thereof.

2. The process of claim 1, wherein the crystalline 2-fluoro-3-nitrotoluene of formula (I) has a DSC onset peak at a value among 25.0 and 26.0° C., DSC maximum peak at a value among 26.0 and 27.5° C., and an X-ray powder diffraction pattern comprising a peak expressed in 2-Theta values (2θ) at 14.3±0.2.

3. The process of claim 1, wherein the crystalline 2-fluoro-3-nitrotoluene of formula (I) has a DSC onset peak at a value between 25.0 and 26.0° C. and an X-ray powder diffraction pattern comprising a peak expressed in 2-Theta values (2θ) at 14.3±0.2.

4. The process of claim 2, wherein the crystalline 2-fluoro-3-nitrotoluene of formula (I) has an X-ray powder diffraction pattern comprising a further peak expressed in 2-Theta values (2θ) at 11.3±0.2.

5. The process of claim 1, wherein the crystalline 2-fluoro-3-nitrotoluene of formula (I) has a DSC onset peak at a value among 25.0 and 25.5° C.

6. The process of claim 1, wherein the crystalline 2-fluoro-3-nitrotoluene of formula (I) has a DSC maximum peak at a value among 26.5 and 27.2° C.

7. The process of claim 1, wherein the crystalline 2-fluoro-3-nitrotoluene of formula (I) has a DSC maximum peak at a value among 26.0 and 27.5° C. and an X-ray powder diffraction pattern comprising a peak expressed in 2-Theta values (2θ) at 14.3±0.2.

8. The process of claim 1 wherein the crystalline 2-fluoro-3-nitrotoluene of formula (I) has an X-ray powder diffraction pattern comprising a further peak expressed in 2-Theta values (2θ) at 11.3±0.2.

9. The process of claim 3 wherein the crystalline 2-fluoro-3-nitrotoluene of formula (I) has an X-ray powder diffraction pattern comprising a further peak expressed in 2-Theta values (2θ) at 11.3±0.2.

10. The process of claim 7 wherein the crystalline 2-fluoro-3-nitrotoluene of formula (I) has an X-ray powder diffraction pattern comprising a further peak expressed in 2-Theta values (2θ) at 11.3±0.2.

11. The process of claim 2, wherein the crystalline 2-fluoro-3-nitrotoluene of formula (I) has a DSC onset peak at a value among 25.0 and 25.5° C.

12. The process of claim 3, wherein the crystalline 2-fluoro-3-nitrotoluene of formula (I) has a DSC onset peak at a value among 25.0 and 25.5° C.

13. The process of claim 2, wherein the crystalline 2-fluoro-3-nitrotoluene of formula (I) has a DSC maximum peak at a value among 26.5 and 27.2° C.

14. The process of claim 7, wherein the crystalline 2-fluoro-3-nitrotoluene of formula (I) has a DSC maximum peak at a value among 26.5 and 27.2° C.

15. The process of claim 1, wherein the crystalline 2-fluoro-3-nitrotoluene of formula (I) has a DSC onset peak at a value among 25.0 and 25.5° C., a DSC maximum peak at a value among 26.5 and 27.2° C., an X-ray powder diffraction pattern comprising a peak expressed in 2-Theta values (2θ) at 14.3±0.2 and a peak expressed in 2-Theta values (2θ) at 11.3±0.2.

16. The process of claim 1, wherein the crystalline 2-fluoro-3-nitrotoluene of formula (I) has a DSC onset peak at a value among 25.0 and 25.5° C. and an X-ray powder diffraction pattern comprising a peak expressed in 2-Theta values (2θ) at 14.3±0.2 and a peak expressed in 2-Theta values (2θ) at 11.3±0.2.

17. The process of claim 1, wherein the crystalline 2-fluoro-3-nitrotoluene of formula (I) has a DSC maximum peak at a value among 26.5 and 27.2° C. and an X-ray powder diffraction pattern comprising a peak expressed in 2-Theta values (2θ) at 14.3±0.2 and a peak expressed in 2-Theta values (2θ) at 11.3±0.2.

\* \* \* \* \*